United States Patent [19]

Corby, Jr. et al.

[11] Patent Number: 5,579,241
[45] Date of Patent: Nov. 26, 1996

[54] REAL-TIME ACQUISITION AND ARCHIVING SYSTEM FOR MULTIPLE TIME-SAMPLED SIGNALS

[75] Inventors: Nelson R. Corby, Jr., Scotia; Richard A. Hogle, Schenectady, both of N.Y.

[73] Assignee: General Electric Company, Schenectady, N.Y.

[21] Appl. No.: 267,623

[22] Filed: Jun. 29, 1994

[51] Int. Cl.$^6$ .............................. G06T 12/40; G09G 5/14
[52] U.S. Cl. .......................... 364/550; 364/578; 128/709; 395/119
[58] Field of Search ........................... 364/550, 578; 382/870.06, 870.21, 870.28, 870.44; 356/376, 375; 128/731, 709

[56] References Cited

U.S. PATENT DOCUMENTS

| | | | |
|---|---|---|---|
| 4,258,421 | 3/1981 | Juhasz et al. | 364/424 |
| 4,523,191 | 6/1985 | Cretin et al. | 340/825.52 |
| 4,951,674 | 8/1990 | Zanakis et al. | 128/653 R |
| 4,965,840 | 10/1990 | Subbarao | 382/1 |
| 5,291,888 | 3/1994 | Tucker | 128/644 |
| 5,515,301 | 5/1996 | Corby, Jr. et al. | 364/578 |
| 5,524,258 | 6/1996 | Corby, Jr. et al. | 395/800 |

*Primary Examiner*—James Trammell
*Assistant Examiner*—Kamini Shah
*Attorney, Agent, or Firm*—Lawrence P. Zale; Marvin Snyder

[57] ABSTRACT

Time sampled data from many hundreds of sensors spatially arranged on a subject is acquired, displayed and archived in real-time. A redundant array of acquisition processors coupled to temporary storage device are controlled by a system control processor. As the data is acquired, an operator interacts with a display processor to select sensors mapped on a computer model of the subject. The selected sensors are displayed as real-time 'postage stamp' traces each located in a position reflecting their position on the subject. During acquisition in the background, or at some time later, the acquired data is archived onto a slower, but much larger data storage device such as a stream tape, or optical disk.

2 Claims, 1 Drawing Sheet

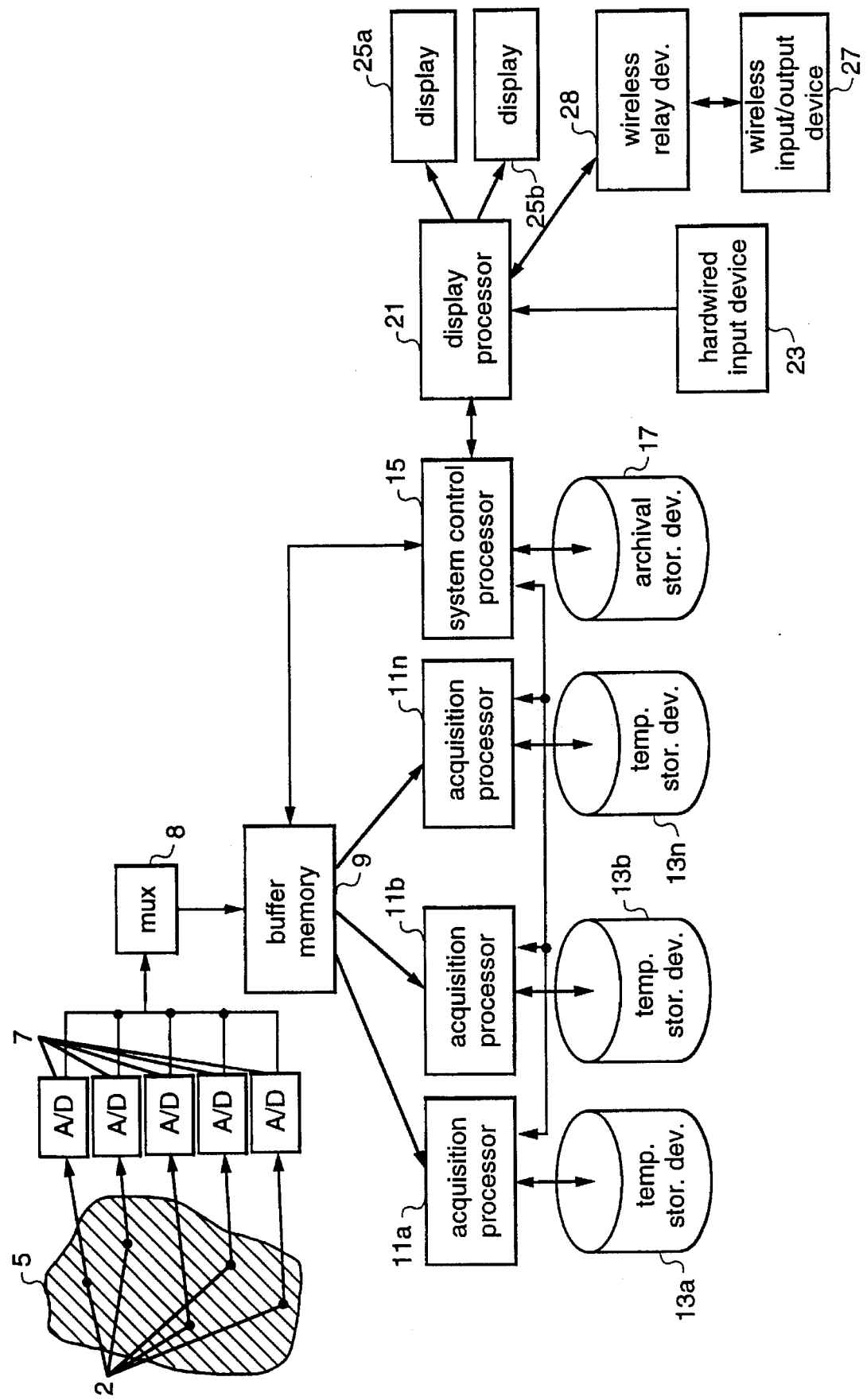

REAL-TIME ACQUISITION AND ARCHIVING SYSTEM FOR MULTIPLE TIME-SAMPLED SIGNALS

CROSS REFERENCE TO RELATED APPLICATIONS

This invention is related to U.S. patent applications Ser. No. 08/268,343, filed Jun. 29, 1994 "Real-Time Processing of Packetized Time-sampled Signals Employing a Systolic Array" by N. Corby, P. Miller, now U.S. Pat. No. 5,524,258; and Ser. No. 267,622, filed Jun. 29, 1994, "Real-Time Visualization System for Multiple Time Sampled Signals" by N. Corby, C. Nafis, P. Miller, now U.S. Pat. No. 5,515,301; both assigned to the present assignee and hereby incorporated by reference.

BACKGROUND OF INVENTION

1. Field of the Invention

The present invention relates to a system for acquiring, display and archiving digital time sampled signals, and more particularly, for a system which acquires, displays and archives data from a large number of sensors.

2. Description of Related Art

There exist many systems which consist of arrays of transducers, or sensors, which are arranged in a complex spatial arrangement and for which digitized representations of the signals has to be acquired, monitored and ultimately archived for later use. Acquisition is the process of moving the sampled, digitized data from a sensor onto some type of temporary storage device. Monitoring is the process of viewing a representation of the data and possibly verifying that the data is of good quality. Archiving is the process of storing the acquired data onto a permanent (usually removeable) medium like magnetic disk or tape or optical disks.

Common examples of such systems include vibration testing systems having arrays of accelerometers, temperature mapping systems having arrays of thermocouples and medical instruments such as electrocardiographic body surface potential measurement system. Another medical system is a magnetic source imaging system which uses a complex arrangement of hundreds of superconducting coils arranged over the chest of patient, known as magnetocardiography, or over the head of a patient known as magnetoencephalography. In these systems, it is necessary to perform the three functions of acquisition, monitoring and archiving.

Typically each sensor produces an analog, time-varying signal. These are usually digitized and stored on an archive device. Since there are many sensors in these systems, data rates for acquisition in real-time exceed the data rate of archive devices. The use of faster archive devices becomes increasingly more expensive, and a limiting factor for real-time archiving.

When hundreds, or thousands, of sensors are involved, it becomes very difficult to select or to jointly view the signal from selected sensors. Usually some method is provided to choose signals for display by, for example, entering channel numbers, each related to a specific sensor, or a group of sensors. Typically, a few dozen waveforms are arranged one above the other. These may be viewed on a stripchart or stripchart-like device. These devices produce waveforms on paper that create a plot of a given signal value versus time. The paper continuously runs through the recorder showing the signals as they vary over time. Typically, the individual traces are assigned differing colors.

Another device which may be used to display the selected signals is a cathode my tube (CRT) display. On a CRT display, the usual solution involves a scrolling-type display, in which the waveforms appear to enter from one side of the display window, slide sideways through the window at a constant rate and then disappear out the side opposite to which they entered.

This fixed arrangement of traces on the stripchart or CRT display does not allow the viewer or operator of the system to appreciate the inter-relation of signals caused by the physical placement of sensors. In order to understand or further process the acquired data, one must appreciate the relative positioning of the sensors which are producing the signals being monitored.

Another problem involves interaction between the system operator and the viewing/acquisition system. Typically, the operator must be able to move around the piece of equipment under test or around the patient in a medical system. With standard operator input devices, the operator has to continually return to the display console to adjust the system parameters or the display parameters.

Thus, there is a need to acquire data, temporarily store the acquired data, display the data and archive the data in such a way that the acquisition of new data is not impeded.

BRIEF DESCRIPTION OF THE DRAWINGS

The features of the invention believed to be novel are set forth with particularity in the appended claims. The invention itself, however, both as to organization and method of operation, together with further objects and advantages thereof, may best be understood by reference to the following description taken in conjunction with the accompanying drawing(s) in which:

FIG. 1 is a diagram of a system for acquiring, monitoring and archiving time-sampled signals from an array of transducers.

SUMMARY OF THE INVENTION

According to the present invention, a system for the acquisition, monitoring and archiving of time sampled samples from a spatial arrangement of sensors includes a buffer memory to temporarily buffer incoming data samples, a number of dedicated acquisition processors having access to the temporary buffer memory coupled to storage device, a system control processor coupled to an archive storage device to coordinate the actions of the dedicated acquisition processors, a display processor with hardwired and wireless remote operator input/output devices and one or more CRT display devices.

Data flowing in from a sensor array is temporarily buffered by the buffer memory and flows through a previously idle dedicated acquisition processor to its attached storage device. Copying continues until the storage device is full or the operator stops the process. Archive storage of the acquired data can then begin over a private path from the selected acquisition processor to the archive storage device attached to the system control processor. While archiving is in progress, another of the dedicated acquisition processors collects the next set of data.

The system control processor routes selected data samples from the buffer memory to the display processor which creates sequences of image data which are viewed on one or more displays attached to the display processor. Hardwired input devices and wireless input devices attached to the display processor allow the operator to interact with the display processor and to affect the actions of the system control processor.

DETAILED DESCRIPTION OF THE INVENTION

In FIG. 1, a plurality of sensors 2 monitor a subject 5. Sensors 2 are sampled by a plurality of analog-to-digital (A/D) converters 7. Digital samples from A/D converter 7 are arranged into a packet of information by a multiplexer ("mux") 8 and temporarily stored in a buffer memory 9 which is preferably a first in first out (FIFO) memory. A plurality of acquisition processors 11a, 11b, . . . 11n are responsive to a system control processor 15. Upon activation, acquisition processors 11 remove data packets from buffer memory and store them on a fast temporary storage device 13a, 13b, . . . 13n, respectively. The system control processor 15 is also attached to the buffer memory. As data begin to accumulate in the buffer memory, system control processor 15 assigns an idle acquisition processor to remove data (at appropriate intervals) and write the data into its attached storage device 13. If the volume of data to be acquired exceeds the capacity of the attached storage device, system control computer 15 may assign a second acquisition processor to continue acquisition. Eventually the operator may choose to halt acquisition or the total acquisition capacity of all attached storage devices may become exceeded. System control processor 15 causes the dedicated archiving processors to copy data from temporary storage devices 13 over a private pathway, to system control processor 15 and onto an archive storage device 17. This may be done as a background process. Typically the transfer speed into the archive storage unit is only a fraction of the original data rate from the sensor, so that archiving time will be some multiple of the acquisition time. Archive storage device 17 does not need to be very fast but must have a very large capacity. It may be large capacity magnetic, optical or magneto-optical disk drive with removable media or may be a digital magnetic tape cartridge. While archiving is in progress, another of the remaining acquisition processors 11 collects the next set of data. Since the acquisition processor does not erase data on temporary storage device 13 until archiving onto the archive storage unit is complete, there is 100% redundancy.

A display processor 21 is coupled to system control processor 15, a set of hardwired operator input devices 23, one or more cathode ray tube-type (CRT) displays and a wireless, non-hardwired operator input/output device 27, which may be a hand-held remote control.

Display processor 21 accepts operator input commands via the hardwired and wireless input/output devices 23 and 27, respectively, and creates the sequence of images that are displayed on display(s) 25a, 25b attached to the display processor. Wireless input/output device 27 may also have a means of displaying signals sent to it from display processor 21 allowing an operator to monitor the system remotely. System control processor 15 controls the low level details of the actual acquisition process, such as monitoring the buffer memory for the arrival or accumulation of data, assigning specific acquisition processors for temporary storage of incoming data, sequencing data flow from the acquisition processor storage devices to the archive storage unit and also selects and routes data from buffer memory 9 to the display processor 2 1 for display.

Hardwired input devices 23 such as a mouse, keyboard, light pen and touch screen attached to display processor 21 allow the operator to interact with display processor 21 and to affect the actions of system control processor 15. Display processor 21 has a wireless relay device 28 attached to it that receives coded transmissions from a hand-held remote control 27 carried by the operator and also transmits visual or graphical data to a display on the hand-held remote control 27. Remote control 27 has buttons for control, keys for data input, and a small display screen for visual review.

While only certain preferred features of the invention have been illustrated and described herein, many modifications and changes will occur to those skilled in the art. It is, therefore, to be understood that the appended claims are intended to cover all such modifications and changes as fall within the true spirit of the invention.

What is claimed is:

1. A data acquisition, display and archive device for processing data from a plurality of sensors spatially arranged on a subject comprising:

a) a buffer memory for receiving and storing the data;

b) a plurality of temporary acquisition branches connected in parallel, each branch comprising:
      1. a temporary storage device capable of storing data,
      2. an acquisition processor coupled to the temporary storage device for reading data from the buffer memory, storing the data on the temporary storage device, emptying the buffer memory and for reading the data from the temporary storage device;

c) an archive storage device capable of storing large amounts of data; and d) a system control processor coupled to each acquisition processor by a control line, for sensing when the buffer memory requires emptying, and for activating an acquisition branch to empty the buffer memory, the system control processor also activating an acquisition branch to download data from its connected temporary storage device to the archive storage device, providing output of status of the system and data stored, the system control processor being responsive to operator input.

2. The data acquisition, display and archive device of claim 1 further comprising:

a) a wireless input/output device for providing operator input to the system control processor, and for displaying output of the remainder of the system;

b) a wireless relay device coupled to the display processor for receiving operator input from the wireless input/output device and provided the operator input to the display processor and ultimately to the system control computer, and for providing system output from the system control computer to the wireless input/output device for display.

* * * * *